United States Patent
Am Ende et al.

(10) Patent No.: US 7,771,748 B2
(45) Date of Patent: Aug. 10, 2010

(54) PHARMACEUTICAL COMPOSITIONS OF 5,7,14-TRIAZATETRACYCLO[10.3.1.0$^{2,11}$.0$^{4,9}$]-HEXADECA-2(11),3,5,7,9-PENTAENE

(75) Inventors: Mary T. Am Ende, Waterford, CT (US); Michael C. Roy, Groton, CT (US); Scott W. Smith, San Diego, CA (US); Kenneth C. Waterman, East Lyme, CT (US); Sara Kristen Moses, Mystic, CT (US)

(73) Assignee: Pfizer Inc, New York, NY (US)

( * ) Notice: Subject to any disclaimer, the term of this patent is extended or adjusted under 35 U.S.C. 154(b) by 1073 days.

(21) Appl. No.: 10/300,608

(22) Filed: Nov. 20, 2002

(65) Prior Publication Data

US 2003/0180360 A1 Sep. 25, 2003

Related U.S. Application Data

(60) Provisional application No. 60/334,652, filed on Nov. 30, 2001.

(51) Int. Cl.
A61K 9/30 (2006.01)
(52) U.S. Cl. .................. 424/475; 424/464; 424/474
(58) Field of Classification Search .............. None
See application file for complete search history.

(56) References Cited

U.S. PATENT DOCUMENTS

| | | | | |
|---|---|---|---|---|
| 4,519,801 | A | | 5/1985 | Edgren |
| 4,943,435 | A | * | 7/1990 | Baker et al. ............ 424/448 |
| 4,983,401 | A | * | 1/1991 | Eichel et al. ............ 424/473 |
| 5,030,452 | A | * | 7/1991 | Curatolo ............ 424/450 |
| 5,030,455 | A | * | 7/1991 | Andoh et al. ............ 424/468 |
| 5,202,128 | A | * | 4/1993 | Morella et al. ............ 424/469 |
| 5,501,861 | A | | 3/1996 | Makino et al. |
| 5,612,059 | A | * | 3/1997 | Cardinal et al. ............ 424/495 |
| 5,698,220 | A | | 12/1997 | Cardinal et al. |
| 5,736,159 | A | | 4/1998 | Chen et al. |
| 5,948,751 | A | * | 9/1999 | Kimer et al. ............ 514/4 |
| 6,036,973 | A | | 3/2000 | Guittard et al. |
| 6,190,696 | B1 | * | 2/2001 | Groenewoud ............ 424/464 |
| 6,306,436 | B1 | * | 10/2001 | Chungi et al. ............ 424/464 |
| 6,410,550 | B1 | | 6/2002 | Coe et al. |
| 6,605,610 | B1 | | 8/2003 | Coe et al. |
| 6,641,840 | B2 | | 11/2003 | Am Ende et al. |
| 6,887,884 | B2 | | 5/2005 | Coe et al. |
| 7,144,882 | B2 | | 12/2006 | Coe et al. |
| 7,205,300 | B2 | | 4/2007 | Coe et al. |
| 2004/0235850 | A1 | | 11/2004 | Waterman |
| 2007/0248671 | A1 | | 10/2007 | Johnson et al. |

FOREIGN PATENT DOCUMENTS

| | | |
|---|---|---|
| EP | 0251459 | 1/1988 |
| EP | 0253541 | 1/1988 |
| EP | 0365947 | 5/1990 |
| EP | 0378404 | 7/1990 |
| WO | WO9935131 A | 7/1999 |
| WO | WO0100182 | 1/2001 |
| WO | WO0132149 | 5/2001 |
| WO | WO0162736 A | 8/2001 |
| WO | WO02/092089 | 11/2002 |
| WO | WO02/092597 | 11/2002 |
| WO | WO02092089 | 11/2002 |
| WO | WO02092597 | 11/2002 |
| WO | WO03/045437 | 6/2003 |
| WO | WO03/063825 | 8/2003 |
| WO | WO2006/040680 | 4/2006 |

OTHER PUBLICATIONS

Berge et al., 66 S Journal of Pharmaceutical Sciences 1 (1977).*
Wu et al. in AAPS PharmSciTech 2000; 1 (3).*
Herbig et al., Journal of Controlled Release, vol. 35 (1995) pp. 127-136.

* cited by examiner

*Primary Examiner*—Eric E. Silverman
(74) *Attorney, Agent, or Firm*—Gregg C. Benson; Garth Butterfield; Mary J. Hosley

(57) ABSTRACT

The present invention is directed to controlled-release (CR) oral pharmaceutical dosage forms of 5,8,14-triazatetracyclo [10.3.1.0$^{2,11}$.0$^{4,9}$]-hexadeca-2(11),3,5,7,9-pentaene, 1, and pharmaceutically acceptable salts thereof, and methods of using them to reduce nicotine addiction or aiding in the cessation or lessening of tobacco use while reducing nausea as an adverse effect. The present invention also relates to an immediate-release (IR) low dosage composition having a stable formulation with uniform drug distribution and potency.

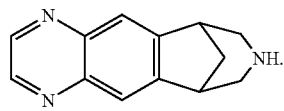

7 Claims, No Drawings

PHARMACEUTICAL COMPOSITIONS OF 5,7,14-TRIAZATETRACYCLO[10.3.1.0$^{2,11}$.0$^{4,9}$]-HEXADECA-2(11),3,5,7,9-PENTAENE

The present invention is directed to controlled-release (CR) oral pharmaceutical dosage forms of 5,8,14-triazatetracyclo[10.3.1.0$^{2,11}$.0$^{4,9}$]-hexadeca-2(11),3,5,7,9-pentaene, 1, and related compounds, and methods of using them to reduce nicotine addiction or aiding in the cessation or lessening of tobacco use while reducing nausea as an adverse effect. The present invention also relates to an immediate-release (IR) low dosage composition having a stable formulation with uniform drug distribution and potency.

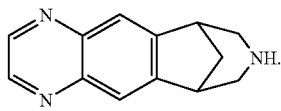

1

BACKGROUND OF THE INVENTION

Compound 1, also known as 7,8,9,10-tetrahydro-6,10-methano-6H-pyrazino[2,3-h][3]-benzazepine, binds to neuronal nicotinic acetylcholine specific receptor sites and are useful in modulating cholinergic function. Accordingly, this compound is useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

Compound 1 and pharmaceutically acceptable acid addition salts thereof are referred to in International Patent Publication WO 99/35131, published Jul. 15, 1999, which is incorporated herein by reference in its entirety.

Whereas immediate release (IR) dosage forms of the aforementioned compound, that is, dosage forms designed to provide the drug in a dissolved form upon swallowing in less than about 30 minutes, provide therapeutically useful levels of drug in the blood and brain, it has been observed that there is a significant level of nausea in patients, especially at doses sufficiently high to be therapeutically useful for some patients. Since nausea can lead to poor patient compliance with a dosing regimen, there is a need to provide 1 in a form that reduces the incidence of nausea.

Accordingly, the present invention provides CR dosage forms of 1 that reduce or eliminate nausea while maintaining a therapeutic level of the drug in the blood and central nervous system (CNS). While examples exist in the art suggesting that CR dosage forms may in some cases provide for a reduction in such side effects as nausea (e.g., oxycodone (J. R. Caldwell, et al., *J. of Rheumatology* 1999, 26, 862-869), venlafaxine (R. Entsuah and R. Chitra, *Psychopharmacology Bulletin*, 1997, 33, 671-676) and paroxetine (R. N. Golden, et al., *J. Clin. Psychiatry*, 2002, 63, 577-584), counter examples also exist which indicate that CR dosage forms are sometimes no better than immediate release dosage forms for the reduction of nausea, and therefore teach away from the utility of the CR form as a means of reducing side effects. Examples of this teaching away include morphine sulfate (T. D. Walsh, et al., *J. Clin. Oncology*, 1992, 15, 268-272), hydromorphone (H. Hays, et al., *Cancer*, 1994, 74, 1808-1816), dihydrocodeine tartrate (G. Xu, et al., *Zhongguo Yaowu Yilaixing Zazhi*, 1999, 8, 52-57) and carbidopa/levodopa (G. Block, et al., *European Neurology*, 1997, 37, 23-27). In addition, in many cases, CR dosage forms result in reduction in bioavailability compared to the IR dosage form, necessitating an increase in dose or even making the use of a CR dosage form infeasible. It therefore remains impossible to predict a priori which drugs showing nausea will actually benefit from CR dosage forms. Moreover, the rate at which the drug is made available, that is, its dissolution rate, can range considerably from slightly slower than the IR dosage form to deliver over an extended period (up to about 24 hours). The inventors have discovered that for 1, CR dosage forms with a certain range of delivery rates will provide therapeutic blood and CNS drug levels while reducing the incidence of nausea when compared to the IR dosage form. The inventors have also discovered specific preferred ways of formulating 1 to achieve the desired drug administration rates. The inventors have also discovered preferred dosing regimens that provide therapeutic drug levels while maintaining low levels of nausea.

The high potency of compound 1 as a nicotinic receptor ligand allows the use of low dosage strengths for administration. For ease of handling, manufacturing and patient convenience, low dosage strength drugs are often formulated at high dilution with excipients. In the preparation and storage of such dilute formulations, however, unique challenges are introduced. First, the high dilution can enable excipients or even excipient impurities to cause significant drug degradation during storage. Examples of excipient properties that may impact drug degradation include moisture content and mobility of moisture (see J. T. Carstensen, *Drug Stability: Principles and Practices*, 2$^{nd}$ Ed, Marcel Dekker, NY, 1995, 449-452)., and excipient acidity affecting local pH microenvironments (see K. Waterman et al., *Pharm Dev. Tech.*, 2002, 7(2), 113-146). Examples of excipient impurities that affect drug degradation include trace metals, peroxides, and formic acid (see K. Waterman, et al., *Pharm. Dev. Tech.*, 2002, 7(1), 1-32). Although consideration of the chemical structure and identification of reactive moieties therein can be used to theorize potential degradation pathways, it remains impossible to predict a priori whether a particular excipient will form an acceptably stable formulation with a given drug. Moreover, 1 has been observed to react with many common excipients and excipient impurities. It therefore remains a need to provide excipient and excipient combinations which can provide acceptable formulations (for such properties as tableting) while providing suitable stability for 1. The inventors have discovered specific preferred ways of formulating 1 to achieve the desired stability. More specifically for a film coated tablet, the inventors have discovered specific formulations and processes to achieve the desired stability.

A second issue sometimes seen with potent drugs prepared at high dilution is variability in potency due to segregation and adhesion to equipment during manufacturing. This issue has been found to be a problem with formulations of 1. One method recently reported for achieving a uniform drug distribution in a blend of a low dose drug makes use of a carrier excipient, lactose, to form an ordered mixture with a micronized drug (L. Wu, et al., *AAPS PharmSciTech,* 2000, 1(3), article 26). Although one can effectively implement a manual brushing step to recover active ingredient segregated by fluidization or adhered to the metal surfaces in small scale equipment, a manual brushing step is neither efficient not desirable in a production scale environment. Liquid processes can minimize the drug loss issues during drug product manufacturing; however, compounds that undergo form changes (e.g. polymorph, hydrate, or solvate changes) make liquid processes very difficult to perform while maintaining drug ingredient stability (physical and chemical). Although many techniques have been used to solve these general problems, it remains impossible to predict which particular techniques will be effective for a given set of drugs and excipients. Therefore, because of the high dilution necessary with 1, there is a need for a process suitable for commercialization of 1 whereby adequate potency uniformity from dosage form (e.g., tablet) to dosage form and lot to lot can be maintained. The inventors have also discovered preferred ways of processing formulations of 1 to achieve the desired uniform drug potency and uniform drug distribution.

SUMMARY OF THE INVENTION

The present invention relates to certain controlled-release (CR) pharmaceutical dosage forms of 1 or pharmaceutically acceptable salts thereof, to a subject in need thereof, said CR dosage form comprising the compound, or pharmaceutically acceptable salt thereof, and a means for delivering the compound, or pharmaceutically acceptable salt thereof, to said subject at a rate of less than about 6 mgA/hour (where mgA refers to milligrams of active drug in equivalence to the free base), whereby at least about 0.1 mgA of the compound, or pharmaceutically acceptable salt thereof, is administered over a 24 hour period. In certain subjects, it may be advantageous, after administration of the CR dosage form in a series of doses, to administer an immediate release (IR) dosage form comprising the compound, or pharmaceutically acceptable salt thereof, as described herein.

In particular, the present invention relates to methods of treatment using CR pharmaceutical dosage forms of 1 that result in a reduction in nausea as an adverse effect. Such CR dosage forms are characterized by providing drug in the gastrointestinal (GI) tract in a dissolved form at a rate ranging from about 0.03 mgA/hr to about 6 mgA/hr; more preferably from about 0.06 mgA/hr to about 3 mgA/hr; and most preferably from about 0.10 mgA/hr to about 1 mgA/hr. The present invention also provides for CR dosage forms which achieve a reduction in the average maximum blood concentration of the drug ($C_{max}$) upon the first administration of the dosage to a subject by between 10 and 80% of the average $C_{max}$ for an immediate release bolus initial administration; more preferably, between 30 and 70%. The present invention also provides for dosage forms which increase the time it takes to achieve this maximum blood level concentration, $T_{max}$. In particular, it has been found that an increase of the average $T_{max}$ by 50% compared to the average found for an immediate release bolus results in a reduction in nausea. The present invention also provides for a dosage form whereby the release rate of 1 as determined by a USP type II dissolution method results in a release rate of less than 6 mgA/hr and such that the time for dissolution of 50% w:w of said drug is between 1 and 15 hours; more preferably between 2 and 10 hours.

The present invention also provides for pharmaceutical compositions to achieve these delivery rates. In particular, the present invention relates to dosage forms of 1 which comprise such means of delivery as hydrophilic matrixes, hydrophobic matrixes, coated CR tablets and multiparticulates, buccal systems, transdermal systems, suppositories and depot systems. Among the coated tablets, a particularly preferred dosage form is an asymmetric membrane technology system (as described in U.S. Pat. Nos. 5,612,059 and 5,698,220, the contents of which are hereby incorporated herein by reference).

The present invention further provides such a controlled release dosage form which is a combination delayed plus sustained release form exhibiting a delay period of up to eight hours prior to the onset of sustained release, wherein the pentaene is released at a rate of not more than about 0.1 mgA/hr during the delay period and wherein the delay period is controlled temporally or spatially by position in the gastrointestinal tract.

It is also the purpose of the present invention to provide for the reduction in nausea when compound 1 is dosed to patients by beginning a course of treatment with the CR dosage form, followed by a course of treatment with an IR dosage form.

As used herein, the term "controlled-release" (CR) refers to dosage forms which slowly release or deliver the drug to the patient at a rate such that at least some of the drug is unavailable in the first hour. A CR system can provide the drug at a constant rate (zero order), at a steadily decreasing rate (first order) or an uneven or pulsatile rate. The drug delivery can also involve a lag time in initial drug release. This lag can be temporal or be related to the position of the drug in the body. For example, a CR dosage form may be prepared by exploiting an enteric coating where drug is released upon reaching the pH of the intestine after oral administration.

In the present invention, a suitable CR dosage form of 1 can be identified by one or both of two methods:

(1) The first method involves measuring the behavior of the drug in the dosage form by sampling and analyzing blood after initial administration of the drug to a subject (generating a pharmacokinetic profile). Initial administration refers to drug administered to a subject either for the first time, or with at least four days since a previous dosing of any form of 1. It has been found that of particular importance in reducing nausea with 1 are the maximum blood level of 1 reached after initial administration of the drug ($C_{max}$) and the time it takes to reach that maximum ($T_{max}$). In measuring both $C_{max}$ and $T_{max}$, it will be recognized by those skilled in the art that there is significant variability between dosings and between subjects. To achieve an adequate comparison in $C_{max}$ and $T_{max}$ and thereby to determine if a given dosage form will achieve the desired reduction in nausea, it is necessary to measure these parameters for at least 10 subjects in a cross-over experiment (i.e., each subject receives both dosage forms, IR and CR) with at least 7 days between experimental legs. In particular, it has been found that an average initial $C_{max}$ reduction to achieve a value of 10 to 80% of that achieved with an average initial IR bolus administration is needed for nausea reduction; more preferred is between 30 and 70%. For $T_{max}$, an increase in the average initial $T_{max}$ for a CR dosage form compared to an IR bolus should be at least 50% (i.e., 1.5 times the number of hours for the average CR dosage vs. the average IR bolus dosage).

(2) The second method of analyzing the CR dosage form to determine if it will reduce nausea involves an in vitro test. The inventors have found that generating a plot of percent of 1 dissolved vs. time is best used to determine the time required for 50% of the drug to be dissolved. The data needed for generation of this plot is obtained using a standard USP (United States Pharmacopoeia) Type II dissolution apparatus (50 rpm; 500 mL of 0.01 N hydrochloric acid; 37° C.) such as a Hanson model SR8. Analysis of samples is accomplished using reverse phase HPLC. It has been found that nausea is reduced when the dosage form shows 50% w/w of the total dose is dissolved between about 1 and 15 hours; more preferably between 2 and 10 hours.

Accordingly, the present invention further relates to immediate-release dosage forms suitable for administration to a subject that result in stable dosage forms with uniform drug distribution and potency, comprising a core containing a compound of the formula 1, or a pharmaceutically acceptable salt thereof, and a pharmaceutically acceptable substantially reducing carbohydrate—free diluent. The invention specifically provides such an immediate-release dosage form, wherein the IR dosage form comprises either the L-tartrate or citrate salt of 5,8,14-triazatetra-cyclo[$10.3.1.0^{2,11}.0^{4,9}$]-hexadeca-2(11),3,5,7,9-pentaene.

As used herein, "substantially reducing carbohydrate-free" means less than approximately 20 w/w % of a reducing carbohydrate (including, but not limited to, lactose). Preferably, dosage forms prepared in accordance with the present invention will contain less than 10 w/w % of a reducing carbohydrate, and more preferably, less than 5 w/w %.

The immediate release dosage form of the invention may further comprise a glidant, disintegrant and/or a lubricant. The present invention also relates to processes for the production of these immediate release dosage forms.

The immediate release dosage form of the invention may further comprise a film coating. The present invention also relates to processes for production of these film coated immediate release dosage forms.

The present invention also provides a formulation suitable for film coating of immediate release dosage forms of 1 wherein the polymeric binder for such coatings comprises substantially a cellulosic polymer. A particularly preferred cellulosic polymer is hydroxypropyl methylcellulose (HPMC). This coating further comprises an opacifier (particularly titanium dioxide), plasticizer and/or glidant, all of which contain less than about 20% w:w reducing carbohydrates. Particularly preferred coating formulations comprise HPMC, titanium dioxide, and triacetin or PEG.

The present invention also provides for methods that produce good potency and content uniformity in blends as described herein. These methods include the process of geometric dilution of drug with excipients prior to tableting. These methods also include the use of moderate shear blending. The preferred blending process uses a "bin blender"; however, other blenders which produce similar shears are also usable.

The disclosed methods of treatment using CR pharmaceutical dosage forms of 1 that result in a reduction in nausea as an adverse effect are characterized by providing drug in the gastrointestinal (GI) tract in a dissolved form at a rate ranging from about 0.03 mgA/hr to about 8 mgA/hr; more preferably from about 0.06 mgA/hr to about 3 mgA/hr; and most preferably from about 0.10 mgA/hr to about 1 mgA/hr.

In particular, the present invention provides a method for reducing nicotine addiction or aiding in the cessation or lessening of tobacco use in a subject, comprising administering to said subject an amount of either the controlled release dosage form or the immediate-release dosage form of 1 that is effective in reducing nicotine addiction or aiding in the cessation or lessening of tobacco use. The invention specifically provides such a method, wherein the CR or IR dosage form comprises either the L-tartrate or citrate salt of 5,8,14-triazatetra-cyclo[$10.3.1.0^{2,11}.0^{4,9}$]-hexadeca-2(11),3,5,7,9-pentaene.

The present invention further provides a method for treating a disorder or condition selected from inflammatory bowel disease, ulcerative colitis, pyoderma gangrenosum, Crohn's disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions; dependencies on, or addictions to, nicotine, tobacco products, alcohol, benzodiazepines, barbiturates, opioids or cocaine; headache, stroke, traumatic brain injury (TBI), obsessive-compulsive disorder (OCD), psychosis, Huntington's Chorea, tardive dyskinesia, hyperkinesia, dyslexia, schizophrenia, multi-infarct dementia, age related cognitive decline, epilepsy, petit mal absence epilepsy, senile dementia of the Alzheimer's type (AD), Parkinson's disease (PD), attention deficit hyperactivity disorder (ADHD) and Tourette's Syndrome in a subject in need of such treatment, comprising administering to the subject an amount of either the controlled release dosage form or the immediate-release dosage form of 1 that is effective in treating such disorder or condition. The invention specifically provides such a method, wherein the CR or IR dosage form comprises either the L-tartrate or citrate salt of 5,8,14-triazatetra-cyclo[$10.3.1.0^{2,11}.0^{4,9}$]-hexadeca-2(11),3,5,7,9-pentaene.

The present invention also provides for pharmaceutical compositions to achieve these administration rates. In particular, the present invention relates to dosage forms of 1 which comprise such means of administration as hydrophilic matrixes, hydrophobic matrixes, osmotic systems, multiparticulates, permeable-coating controlled dosage forms, suppositories, buccal systems, transdermal systems and implantable systems. Among the osmotic systems, a particularly preferred dosage form is an asymmetric membrane technology system (as described in U.S. Pat. Nos. 5,612,059 and 5,698,220, the contents of which are incorporated herein by reference).

The present invention also provides for methods of administration which result in the reduction in nausea as an adverse effect when compound 1 is dosed to patients by beginning a course of treatment with the CR dosage form, followed by a course of treatment with an IR dosage form.

As used herein, an "immediate-release" (IR) dosage form refers to a dosage form which when taken orally substantially provides the drug in a form available to be absorbed within about one hour.

A "matrix" system refers to a particular CR dosage form where the drug is admixed with excipients, often in compressed or extruded form, such that the release of the drug from the dosage form is controlled by a combination of erosion and diffusion. Erosional control of drug delivery involves the slow removal of the matrix material by the GI fluids to gradually expose and release the drug from the matrix. Diffusional control of drug delivery involves diffusion of soluble drug through the network of matrix excipients in a controlled fashion. In practice, many matrix dosage forms involve some degree of combination of the two mechanisms.

A "hydrophilic matrix" is a matrix CR dosage form where water-soluble or water-swellable polymers form a network containing the drug. The rate that drug diffuses to the surface of the dosage form and the rate that the matrix falls apart control the rate that drug is made available to the GI system.

A "hydrophobic matrix" is a matrix CR dosage form where water-insoluble or only partially water-soluble materials slow the rate that a drug is exposed to the fluid environment of the GI system, thereby controlling the rate drug is available for absorption.

A "permeable coating" CR system refers to various coatings on tablets or particulates that act as barriers to drug leaving a tablet or to water reaching the drug. These coatings include enteric coatings which become permeable as the pH increases when a dosage form exits the stomach. Examples of such coatings include Eudragits™ sold by Rohm GmbH Pharma Polymers (Darmstadt, Germany) and cellulose acetate hydrogen phthalate (CAP) sold by Eastman Chemical (Kingsport, Tenn.). One group of such coated CR systems includes osmotic systems. Such CR dosage forms involve a semi-permeable membrane surrounding a drug core containing sufficient osmotic pressure to drive water across the membrane in the GI system. The osmotic pressure can then force drug out of the core through preformed or in situ produced holes or pores in the coating. Such systems often involve the addition of agents (osmagents) designed to increase the osmotic pressure in the core. A review describing such systems is found in G. Santus and R. W. Baker, *J. Control. Rel.*, 1995, 35, 1-21.

"Asymmetric membrane technology," AMT, describes a particular osmotic CR system where the coating is made porous by a phase separation process during the coating operation as described in U.S. Pat. Nos. 5,612,059 and 5,698,220, the contents of which are hereby incorporated herein by reference.

"Transdermal delivery systems" are drug delivery devices designed to provide systemic drug to a patient through the skin. Such systems commonly involve a layer of material containing drug on a backing with an adhesive to attach the material to the subject's skin.

"Buccal delivery systems" are dosage forms which provide a method for drug absorption through the buccal (inner cheek) tissue.

A "depot" is a controlled-release drug dosage form where a drug and appropriate excipients are injected either subcutaneously or intramuscularly and form a mass (matrix) which slowly provides drug to the systemic circulation.

The drug, 1, for the purposes of the present invention refers to the parent drug and all pharmaceutically acceptable salts and prodrugs, thereof.

The term "mgA" refers to the number of milligrams of active drug based on the free base form of the drug.

The phrase "pharmaceutically acceptable" indicates that the substance or composition must be compatible chemically, physically, and/or toxicologically, with the other ingredients comprising a formulation, and/or the mammal being treated therewith.

The term "active ingredient" refers to a therapeutically active compound, as well as any prodrugs thereof and pharmaceutically acceptable salts, hydrates, and solvates of the compound and the prodrugs.

The term "appropriate period of time" or "suitable period of time" refers to the period of time necessary to achieve a desired effect or result. For example, a mixture may be blended until a potency distribution is reached that is within an acceptable qualitative range for a given application or use of the blended mixture.

As used herein, the term "unit dose" or "unit dosage" refers to a physically discrete unit that contains a predetermined quantity of active ingredient calculated to produce a desired therapeutic effect. The unit dose or unit dosage may be in the form of a tablet, capsule, sachet, etc. referred to herein as a "unit dosage form."

DETAILED DESCRIPTION OF THE INVENTION

Procedures for making compound 1 are described in U.S. Pat. No. 6,410,550, the contents of which are hereby incorporated herein by reference, and the resolution of racemic mixtures thereof is described in WO01/62736. In accordance with the present invention, the CR pharmaceutical compositions of 1 can be desirably administered in doses ranging from about 0.1 mgA up to about 6 mgA per day, more preferably from about 0.5 to 4 mgA/day, and most preferably from about 1 to 4 mgA per day in single or divided doses, although variations will necessarily occur depending upon the weight and condition of the subject being treated. Depending on individual responses, dosage levels below the lower limit of the aforesaid range may be more than adequate, while in other cases still larger doses may be employed without causing any harmful side effects.

Although any pharmaceutically acceptable form of 1 may be used in connection with the present invention, it is preferable to use a salt form of the drug. A particularly preferred salt form of the drug is the L-tartrate salt.

To control nausea using a CR dosage form of 1, the release rate of the drug must be such that the drug is metered into the GI system in a form available for drug absorption at a rate significantly slower than that for the IR dosage form. Using divided IR dosages in a clinical trial, it was found that if the drug is released at a rate corresponding to about 12 mgA/hr (for a total dose of 3 mgA), the incidence of nausea reports exceeded 50% of the subjects tested. In contrast, at a dosing rate corresponding to about 8 mgA/hr (for a total dose of 2 mgA) the incidence level for nausea dropped to about 13%. This therefore determines an upper limit of 8 mgA/hr for the rate of drug administration needed for a CR dosage form to reduce nausea. In view of the present invention, it is anticipated that even greater improvement in nausea reduction will result by use of slower release rates. Oral CR dosage forms can generally be expected to undergo not more than about 18 hours of drug absorption, depending on the motility of the dosage form for the individual. Based on the blood levels of the drug needed for efficacy, it is anticipated that the total dose required for the drug is about 0.5 mgA to 6 mgA per day. Based on this, the lower limit on the rate of drug administration is approximately 0.03 mgA/hr. Although these extremes would certainly provide for the benefits described in the present invention, the inventors have found that to achieve the desired therapeutic blood levels while maintaining the nausea reduction, the drug is administered at a rate of between about 0.06 and 3 mgA/hr; and more preferably between 0.1 and 1 mgA/hr.

A number of means have been found to produce such a CR system to achieve the desired rate of drug administration. Examples of such means are set forth in International Patent Publications WO02/17918 and WO99/01121, both of which are hereby incorporated by reference. One such means is a matrix. In particular, a matrix tablet or matrix multiparticulates of 1 can be prepared in accordance with this invention. In the case of multiparticulates, the final presentation of the dosage form can be made by adding the particulates to a capsule or providing a sachet or other such presentation. These matrix dosage forms can be formed using traditional techniques such as by compression with a tablet press or by such processes as extrusion/spherinization, roto-granulation or melt congealing. Multipartiulcates can also provide for controlled-release drug delivery behavior by coatings that control the diffusion of drug. Such coatings can restrict water and drug permeability or have solubilites such that they are removed after a particular time or at a particular pH. Two types of matrix dosage forms are appropriate for 1: hydrophilic and hydrophobic. A hydrophilic matrix matrix formulation generally consists of mixtures of high and low molecular weight water-soluble polymers. In particular, these matrix materials consist of combinations of different molecular weights of hydroxypropylmethylcellulose (HPMC), polyethyleneoxide (PEO), hydroxy-propylcellulose (HPC), polyacrylates, alginate, xantham gum and other such polymers. Particularly preferred polymers include HPMC and PEO. A particularly preferred formulation consists of a mixture of HPMC marketed under the tradename K4M Methocel™ (available from Dow Corp., Midland, Mich.) and calcium phosphate dibasic marketed under the tradename D-tab™ (available from Rhodia Inc., Cranbury, N.J.). Hydrophobic matrix formulations of 1 can be prepared by using hydrophobic materials to slow the rate that water comes in contact with 1, respectively. Particularly preferred hydrophobic materials include carnauba wax, glyceryl behenate and stearic acid. It will, however, be appreciated by those versed in the art that other similar waxy materials will function in an equivalent fashion.

Osmotic dosage forms can also provide the desired release rate for 1. One approach involves two-compartment systems (also known as "push-pull" systems). See, e.g., U.S. Pat. No. 4,111,202. In a push-pull system, the drug or drug formulation is present in one compartment and water-soluble or water-swellable auxiliaries (e.g. salts, sugars, swellable polymers and hydrogels) for producing an osmotic pressure are present in a second compartment. The two compartments are separated from each other by a flexible partition and sealed externally by a rigid water-permeable membrane. Fluids entering the second compartment cause an increase in volume of the lower compartment, which in turn acts on the expanding flexible partition and expels the contents of the drug compartment from the system. The preparation of push-pull systems is technically complicated. For example, a flexible partition consisting of a material different from that of the water-permeable membrane has to be incorporated into the dosage form. In addition, for sparingly soluble high-dosage drugs (e.g. more than 200 mg dose), a push-pull system would be voluminous thus making its ingestion difficult.

Push-pull systems for sparingly soluble drugs without a partition are disclosed in U.S. Pat. No. 4,327,725. A commercial embodiment of this system is known as GITS (gastrointestinal therapeutic system) and is marketed in commercial products such as Procardia™ XL and Glucotrol™ XL (both available from Pfizer, Inc., New York, N.Y.). The core consists of two layers: one layer containing the drug and a second layer containing an osmotic driving member. A rigid water-permeable layer surrounds the core and contains a passageway in communication with the drug layer only. The osmotic driving member is a swellable polymer or hydrogel (e.g., polyethylene oxide). Absorption of fluid into the system causes the hydrogel in the second layer to expand thus forcing the contents of the drug layer through the passageway.

Another approach for delivering drugs in an osmotic tablet is the addition of a gas generating means to the tablet core. U.S. Pat. Nos. 4,036,228 and 4,265,874 disclose a single layer core containing a limited solubility drug, a gas generating means (e.g., effervescent couple), an osmagent and a surfactant having wetting, solubilizing and foaming properties (e.g., sodium lauryl sulfate). Fluids imbibing through a rigid water-permeable membrane surrounding the core causes the gas-generating means to produce a gas which creates a pressure sufficient to expel the drug through an orifice in the membrane.

Another method of delivering drugs osmotically involves the use of single layer osmotic tablets. Such tablets are described in G. Santus and R. W. Baker, *J. Control. Rel.*, 1995, 35, 1-21, incorporated herein by reference. Other single-layer osmotic tablets are described in copending application PC11850, incorporated herein by reference. A particularly preferred osmotic dosage form for 1 is in the form of an AMT system, as described for example in U.S. Pat. Nos. 5,612,059 and 5,698,220. (See, also, S. M. Herbig, *J. Control. Rel.*, 1995, 35, 127-136). Such systems provide for good control of the drug release throughout the GI system. The inventors have found that preferred formulations consist of cores made from the L-tartrate salt of the drug, mannitol, microcrystalline cellulose, dicalcium phosphate and magnesium stearate. These cores can be prepared by direct compression, wet granulation (with a high or low shear wet granulator or fluid bed granulator), extrusion granulation, rotogranulation or roller compaction. Roller compaction is especially preferred due to its ability to prevent drug segregation, while maintaining drug stability (in contrast to aqueous wet granulations which can lead to drug hydrate formation). The tablets can be prepared on standard tablet presses (rotary). The tablet cores are then coated using a pan coater. The coating favorably consists of a mixture of cellulose acetate (CA) and polyethylene glycol (PEG) coated from acetone and water. The ratio of components is selected such that the CA/PEG combination produce a porous, semipermeable coating which administers the drug through the pores in the GI tract at the desired rate. Most preferably, the ratio of CA to PEG is chosen such that the PEG is in a single phase with the CA since phase-separated PEG was found to lead to drug degradation at elevated temperatures in the final dosage form. Phase compatibility for the purpose of this invention can be determined using a standard differential scanning calorimeter on the desired CA to PEG blend. The absence of a PEG melt transition between 30° C. and 50° C. is an indication of a single phase, and therefore, an indication that such a ratio will form a preferred film. It is therefore most preferred that the CA/PEG ratio remain above about 4.

Non-oral CR systems can also provide nausea reduction while maintaining efficacy upon administration of 1. These systems include suppositories, transdermal systems, buccal systems, depots and implantable devices. In order to function to reduce nausea, these devices must provide controlled-release behavior as described previously. A particularly preferred non-oral dosage form is a transdermal dosage form.

With all the CR dosage forms, the drug is preferably delivered at a rate of between about 0.06 and 3 mgA/hr; and more preferably between 0.1 and 1 mgA/hr. Suitability for the present invention can be determined either by in vivo or in vitro testing. In particular, it is preferred that the average initial $C_{max}$ be reduced to achieve a value of 10 to 80% of that achieved with an average initial IR bolus administration; more preferred is between 30 and 70%. For $T_{max}$, an increase in the average initial $T_{max}$ for a CR dosage form compared to an average initial IR bolus is preferred to be at least 50%. Preferred dosage forms for the present invention provide 50% w:w of the total dose into solution between about 1 and 15 hours; more preferably between 2 and 10 hours.

CR systems for the present invention can involve a delay or lag period between when the dose is administered and when drug is available for absorption. Such delays can be temporal or related to the position in the gastrointestinal tract. These systems will be effective for the purposes of the present invention as long as once they begin providing drug for absorption, the rate falls within the limits described above. A particularly preferred delayed release system is an enteric-coated tablet or multiparticulate. Preferred enteric systems can be prepared by coating tablets or multiparticulates with such materials as cellulose acetate phthalate or enteric polyacrylics such as those marketed under the Eudragit brand name (available from Rohm Pharmaceuticals).

Formulations useful for the present invention can be prepared using a wide range of materials and processes known in the art. The inventors have found, however, that the presence of reducing carbohydrates is detrimental to the drug stability on storage. In particular, CR formulations with less than 20% w/w of reducing carbohydrates are preferred; still more preferred are CR formulations with less than 10% w/w reducing carbohydrates; and most preferred are CR formulations with less than 5% w/w reducing carbohydrates. A particular reducing carbohydrate that is preferably avoided is lactose.

For preparation of the controlled release and immediate release dosage forms, the active ingredient may be used per se or in the form of its pharmaceutically acceptable salt, solvate and/or hydrate. The active ingredient may be used per se or in the form of its pharmaceutically acceptable salt, solvate and/or hydrate. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogen-phosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like.

The final pharmaceutical composition is processed into a unit dosage form (e.g., tablet, capsule or sachet) and then packaged for distribution. The processing step will vary depending upon the particular unit dosage form. For example, a tablet is generally compressed under pressure into a desired shape and a capsule or sachet employs a simple fill operation. Those skilled in the art are well aware of the procedures used for manufacturing the various unit dosage forms.

The active blend of an immediate release dosage form generally includes one or more pharmaceutically acceptable excipients, carriers or diluents. The particular carrier, diluent or excipient used will depend upon the means and purpose for which the active ingredient is being applied. In general, an immediate release tablet formulation includes materials such as diluents, binders, lubricants, glidants, disintegrants and mixtures thereof. Although many such excipients are known to those skilled in the art, the inventors have found that only a sub-set of those provide for the most stable formulations. In particular, the inventors have found that preferred formulations contain less than about 20% w:w reducing carbohydrates. Reducing carbohydrates are sugars and their derivatives that contain a free aldehyde or ketone group capable of acting as a reducing agent through the donation of electrons. Examples of reducing carbohydrates include monosaccharides and disaccharides and more specifically include lactose, glucose, fructose, maltose and other similar sugars. The inventors have further found that formulations containing dicalcium phosphate are particularly stable. More specifically, stable formulations are produced with more than about 20% w:w dicalcium phosphate. Other acceptable excipients include starch, mannitol, kaolin, calcium sulfate, inorganic salts (e.g., sodium chloride), powdered cellulose derivatives, tribasic calcium phosphate, calcium sulfate, magnesium carbonate, magnesium oxide, poloxamers such as polyethylene oxide and hydroxypropyl methylcellulose. To ensure content uniformity of the blend, a volume mean diameter drug substance particle size of less than or equal to about 30 microns is preferably utilized. Preferred diluents are microcrystalline cellulose (e.g., Avicel® PH200, PH102 or PH101 available from FMC Pharmaceutical, Philadelphia, Pa.) and calcium phosphate dibasic, or dicalcium phosphate, (e.g. A-Tab® available from Rhodia, Chicago Heights, Ill.). The mean particle size for the microcrystalline cellulose generally ranges from about 90 µm to about 200 µm. Suitable grades of dicalcium phosphate include anhydrous (about 135 to 180 µm mean, available from PenWest Pharmaceuticals Co., Patterson, N.Y. or Rhodia, Cranbury, N.J.), and dihydrate (about 180 µm, available from PenWest Pharmaceuticals Co., Patterson, N.Y. or Rhodia, Cranbury, N.J.). Generally, the microcrystalline cellulose is present in an amount from about 10 wt % to about 70 wt % and the dicalcium phosphate is present in an amount from about 10 wt % to about 50 wt %, more preferably, microcrystalline cellulose is present in an amount of about 30-70 wt % and the dicalcium phosphate is present in an amount of about 20-40 wt %.

If desired, a binder may be added. Suitable binders include substances such as celluloses (e.g., cellulose, methylcellulose, ethylcellulose, hydroxypropyl cellulose and hydroxymethylcellulose), polypropylpyrrolidone, polyvinylprrolidone, gelatin, gum arabic, polyethylene glycol, starch, natural and synthetic gums (e.g., acacia, alginates, and gum arabic) and waxes.

A lubricant is typically used in a tablet formulation to prevent the tablet and punches from sticking in the die. Suitable lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc and zinc stearate. A preferred lubricant is magnesium stearate. The magnesium stearate is generally present in an amount from about 0.25 wt % to about 4.0% wt %.

Disintegrants may also be added to the composition to break up the dosage form and release the compound. Suitable disintegrants include sodium starch glycolate, sodium carboxymethyl cellulose, calcium carboxymethyl cellulose, croscarmellose sodium, polyvinylpyrrolidone, methyl cellulose, microcrystalline cellulose, powdered cellulose, lower alkyl-substituted hydroxypropyl cellulose, polacrilin potassium, starch, pregelatinized starch and sodium alginate. Of these, croscarmellose sodium and sodium starch glycolate are preferred, with croscarmellose sodium being most preferred. The croscarmellose sodium is generally present in an amount from about 0.5 wt % to about 6.0 wt %. The amount of disintegrant included in the dosage form will depend on several factors, including the properties of the dispersion, the properties of the porosigen (discussed below), and the properties of the disintegrant selected. Generally, the disintegrant will comprise from 1 wt % to 15 wt %, preferably from 1 wt % to 10 wt % of the dosage form.

Examples of glidants include silicon dioxide, talc and cornstarch.

A film coating on the immediate release dosage form can provide ease of swallowing, reduction in unpleasant taste or odor during administration, improved photostability through use of an opacifier, improved elegance, reduced friction during high-speed packaging, or as a barrier between incompatible substances (G. Cole, J. Hogan, and M. Aulton, *Pharma-*

*ceutical Coating Technology*, Taylor and Francis Ltd, Ch 1, 1995). When used, the inventors have found that coatings containing a majority of cellulosic polymers provide superior chemical stability for the drug. Cellulosics are polymers derived from cellulose. Examples of polymers include cellulosics such as hydroxypropyl methylcellulose, hydroxypropylcellulose, hydroxyethylcellulose, methylhydroxyethylcellulose, methylcellulose, and sodium carboxymethylcellulose. A preferred polymer is hydroxypropyl methylcellulose. Coatings of the present invention comprise a polymer, an opacifier, a plasticizer a pharmaceutically acceptable diluent/filler and optionally a colorant. An opacifier is an excipient that help decrease the transmission of light through the coating to the core of the tablet. Examples of opacifiers include titanium dioxide and talc. A preferred opacifier is titanium dioxide. A plasticizer is a material which lower the glass transition temperature of the polymer thereby typically improving physical properties. Examples of plasticizers include polyhydric alcohols such as glycerol and polyethylene glycols and acetate esters such as glyceryl triacetate (triacetin) and triethyl citrate. Optionally, the compositions of the present invention may include a colorant. Such colorants are available from a number of commercial vendors and are well known to those skilled in the art. Particularly preferred coating formulations comprise HPMC, triacetin and titanium dioxide or HPMC, PEG and titanium dioxide.

To achieve a uniform distribution of drug in a blend prior to tablet or capsule production, two methods have been invented. In the first method, a geometric dilution process is used. In this process, a pre-blend of the drug and a portion of the excipients is prepared and subsequently further diluted with the remaining excipients in 2-5 additional steps. In the first dilution step, drug is mixed with 10-30 wt % of the excipient(s). In the second dilution, the first pre-blend is further diluted with 10-40 wt % excipient(s). In the third to fifth dilutions, the second dilution blend is further diluted with 10-75 wt % excipient(s) to form the final blend. A preferred dilution scheme involves first diluting the drug with the dicalcium phosphate in two increments, then combining with a blend of the remaining excipients.

The second process for achieving uniform drug distribution involves blending the formulation with a particular level of shear. The inventors have found unexpectedly that shear the is too high or low results in poor uniformity or total potency. The inventors have found that the desirable shear is achieved using either a bin blender or a high shear blender operated at low shear conditions (less than 200 rpm). The typical blending time for the blending in the bin blender is from about 20 minutes to about 30 minutes. Although blending times greater than 30 minutes can be used, care should be taken not to demix the blend. After the initial blending step, the active blend may be sieved using a conical mill (Comil 197, Quadro Engineering, Inc., Waterloo, Ontario, Canada) fitted with a 0.8 mm screen. The lubricant is then added to the active blend and blended for about 3 minutes in the twin shell "V" or bin blender prior to dry granulating.

The processes described above provide efficient mixing and a more uniform distribution of the active ingredient without significant degradation of the active ingredient; however, the loss of active ingredient due to segregation or adherence of the compound to the metal surfaces of the equipment (e.g., screens and vessel surfaces) presented an additional challenge especially for low dosage formulations (e.g., less than 4 mg per unit dose). The inventors have found a third way of attaining acceptable blend potency involves the use of an abrasive excipient, such as dicalcium phosphate. More specifically, preferred formulations contain 10-50 wt % dicalcium phosphate.

The pharmaceutical composition can be used to produce unit dosage forms containing about 0.1 mg to about 10.0 mg active ingredient per unit dosage, preferably, about 0.2 mg to about 5.0 mg active ingredient per unit dosage. The tablet size (i.e., unit dosage form) is typically between about 100 mg and 600 mg.

The tablets are generally prepared by compression in a rotary press. However, the particular method used for tablet formation is non-limiting and is well known to those skilled in the art. After formation of the tablets, the tablets are often coated with one or more coatings. The tablet may be coated with a coating to mask flavor, to act as a sealant and/or to act as a receptor for printing a logo or trademark on the tablet surface. Alternatively, the tablet may be coated with a film-forming protecting agent(s) to modify the dissolution properties of the tablet. For example, the tablet may be coated with a film-forming coating that resists dissolution for a predictable period of time thus resulting in a delayed or prolonged release of the active ingredient. Suitable film-forming protecting agents include celluloses (e.g., hydroxypropyl-methylcellulose, hydroxypropyl cellulose, methylcellulose), polyvinyl pyrrolidone, and ethyl acrylate-methyl methacrylate copolymers. The coating formulations may also include additives such as plasticizers (e.g., polyethylene glycol or triacetin), preservatives, sweeteners, flavoring agents, coloring agents and other known additives to provide an elegant presentation of the drug. A preferred coating formulation contains 40-70 wt % cellulosic polymer(s). Preferably, the aqueous coating of the immediate release dosage form of the present invention comprises Opadry® (YS-1-18202-A) and Opadry Clear® (YS-2-19114-A) manufactured by Colorcon, West Point, Pa. Opadry®, useful as an opacifying coat, contains hydroxypropyl methylcellulose, titanium dioxide, and polyethylene glycol or triacetin. Opadry Clear®, useful as a polish coat, contains hydroxypropyl methylcellulose and triacetin.

The inventors have found that preferred formulations consist of cores made from the L-tartrate salt of the drug, mannitol, microcrystalline cellulose, dicalcium phosphate and magnesium stearate. More preferred formulations consist of cores made from the L-tartrate salt of the drug, microcrystalline cellulose, dicalcium phosphate and magnesium stearate. Even more preferred formulations consist of cores made from the L-tartrate salt of the drug, microcrystalline cellulose, dicalcium phosphate, croscarmellose sodium, silicon dioxide and magnesium stearate. These cores can be prepared by direct compression, wet granulation (with a high or low shear wet granulator or fluid bed granulator), extrusion granulation, rotogranulation or roller compaction. Roller compaction is especially preferred due to its ability to prevent drug segregation, while maintaining drug stability (in contrast to aqueous wet granulations which can lead to drug hydrate formation). The tablets can be prepared on standard tablet presses (rotary). The tablet cores are then coated using a pan coater. The preferred coating consists of a mixture of hydroxypropyl methyl-cellulose, titanium dioxide, polyethylene glycol or triacetin, and optionally a colorant.

Alternatively, the active pharmaceutical blend may be filled into hard shell capsules, also referred to as the dry-filled capsule (DFC). The capsule formulation and manufacturing process is similar to the reported tablet core formulation and manufacturing process. A hard shell capsule could consist of gelatin and water or hydroxypropyl methylcellulose, water and a gelling agent (gelan gum or carageenan).

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The pharmaceutical compositions containing compound 1 described herein are useful in the treatment or prevention of inter alia inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

Accordingly, the pharmaceutical formulations containing compound 1 and processes described herein may be used in the manufacture of a medicament for the therapeutic applications described above.

A therapeutically effective amount of the manufactured medicament may be administered to a human in need of such treatment or prevention. As used herein, the term "therapeutically effective amount" refers to an amount of active ingredient which is capable of inhibiting or preventing the various pathological conditions or symptoms thereof and sequelae, referred to above. The terms "inhibit" or "inhibiting" refers to prohibiting, treating, alleviating, ameliorating, halting, restraining, slowing or reversing the progression, or reducing the severity of a pathological condition or symptom related to or resultant from the respective condition being treated. As such, the pharmaceutical formulations may be used for both medical therapeutic (acute or chronic) and/or prophylactic (prevention) administration as appropriate. The dose, frequency and duration will vary depending on such factors as the nature and severity of the condition being treated, the age and general health of the host and the tolerance of the host to the active ingredient. The pharmaceutical composition or medicament may be given in a single daily dose, in multiple doses during the day or even in a weekly dose. The regimen may last from about 2-3 days to several weeks or longer. Typically, the composition is administered to a human patient once or twice a day with a unit dosage of about 0.25 mg to about 10.0 mg, but the above dosage may be properly varied depending on the age, body weight and medical condition of the patient and the type of administration.

The following examples are provided for illustrative purposes and should not be construed to limit the scope of the present invention.

The following list of materials used in the Examples may be prepared or acquired from the corresponding source:

Compound 1 (L-tartrate salt) may be prepared by the methods described in patent applications WO9935131 A1 or WO0162736A1, incorporated herein by reference.

Microcrystalline cellulose (Avicel™ PH200) available from FMC Pharmaceutical (Philadelphia, Pa.).

Mannitol (granular 2080) available from SPI Polyols, Inc. (New Castle, Del.).

Dialcium phosphate, anhydrous, (A-tab™) available from Rhodia Inc. (Chicago Heights, Ill.).

Croscarmellose Sodium (Ac-Di-Sol™) available from FMC BioPolymer (Philadelphia, Pa.).

Sodium Starch Glycolate (Explotab™) available from Penwest (Patterson, N.J.).

Silicon dioxide, colloidal (Cab-O-Sil™) available from Cabot Corporation (Boston, Mass.).

Silicified Microcrystalline Cellulose (ProSolv™) available from Penwest (Patterson, N.J.).

Hydroxypropyl cellulose (Klucel™) available from Hercules, Inc. (Hopewell, Va.).

Lactose, anhydrous available from Quest International (Norwich, N.Y.).

Magnesium stearate, animal or vegetable source, available from Mallinckrodt (St. Louis, Mo.).

Film coatings, Opadry™ available from (Colorcon, West Point, Pa.).

Cellulose acetate (398-10 NF) available from Eastman Chemicals (Kingsport, Tenn.).

Polyethyleneglycol (PEG3350) available from Union Carbide Corp. (subsidiary of Dow Chemical Co., Midland, Mich.).

Hydroxypropyl methylcellulose (HPMC, K4M, Methocel™) available from Dow Chemical Co., Midland, Mich.

EXAMPLE 1

Preparation of an AMT CR Dosage Form for the L-Tartrate Salt of 1

A 3 kg batch of tableting granulation was prepared as follows: 450 g of microcrystalline cellulose and 1602 g of calcium phosphate dibasic were mixed in an 8-quart V-blender f0 min. Half the blend was discharged into a polyethylene bag, leaving half the blend remaining in the blender. To a 1250-cc glass bottle were added 450 g of mannitol and 10.3 g of the drug. The mixture was blended using a Turbula™ blender (available from Geln Mills Inc., Clifton, N.J.). This material was added to the V-blender containing the above listed materials. An additional 450 g of mannitol were added to the bottle followed by 5 minutes of Turbula blending to rinse any drug from the bottle. This material was also added to the V-blender, and the mixture was blended for 20 minutes. The material that had been discharged to the polyethylene bag was then added to the V-blender and the mixture was blended for an additional 20 min. A 22.5 g aliquot of magnesium stearate was then added to the V-blender and the mixture was blended for 5 min. The mixture was roller compacted using a TF-Mini roller compactor (available from Vector Corp., Marion, Iowa) with DSP rollers, using a roll pressure of 30 kg/cm$^2$, a roll speed of 4.0 rpm and an auger speed of 15.6 rpm. The ribbons formed were milled using an M5A mill (available from Fitzpatrick Corp., Elmhurst, Ill.) with an 18 mesh Conidur rasping screen at 300 rpm. The powder was then placed back in the V-blender, and another 15 g of magnesium stearate were added, followed by an additional 5 min. of blending.

The granulation was tableted using a Kilian T100 (available from Kilian & Co. Inc., Horsham, Pa.) tablet press using ⁹⁄₃₂" (11 mm) SRC tooling to give tablets of 250 mg/tablet (0.5 mgA). The precompression force used was 2.8 kN, the main compression force was 8 kN, running at 74 rpm with a feed paddle speed of 20 rpm. The resulting tablets showed hardnesses of 7-9 kp, with no measurable friability.

The tablets were coated by first preparing a coating solution consisting of 538 g of cellulose acetate and 134.5 g of PEG in 4506 g of acetone and 1547 g of water. Coatings were carried out using an HCT-30EX Hicoater (available from Vector Corp., Marian, Iowa). A spray rate of 20.0 g/min was maintained with an outlet temperature of 28° C. until the target coating weight of 27.5% gain was achieved. The tablets were then tray dried in an oven at 40° C. for 24 hrs.

Tablets showed pH independent dissolution behavior in vitro using USP type II dissolution (37° C., paddles at 50 rpm, analysis by HPLC potency assay). The percent of drug dissolved as a function of time in the dissolution medium were as follows: 2 hrs, 1%; 5 hrs, 8%; 8 hrs, 35%; 10 hrs, 52%; 12 hrs, 65%; 16 hrs, 81%; 24 hrs, 95%. Thus the system delivers 0.03 mg/hr after a 5 hour lag.

EXAMPLE 2

Clinical Trial Results for Nausea using AMT from Example 1

In use of 1 in a clinical single dose study of the IR dosage form with fasting non-smokers, nausea was reported for 50% of subjects (2/4) at a dose of 1 mgA and 75% of subjects (3/4) at a dose of 3 mgA. With multidose studies, 1 mgA per day was well tolerated; however, persistent nausea was sufficiently bad (7/12 subjects) with 2 mgA/day that this study arm was discontinued. In a single dose test of fed, healthy smokers, nausea or related complaints were reported in 2 of 16 subjects given the maximum dose of 2 mgA for the IR. In contrast, a dose of 3 mgA and 4 mgA for the above AMT dosage form resulted in a similar levels of nausea as seen with a lower dose of the IR dosage form (2/16 for each case). In multidose studies, the levels of nausea for 3 mgA AMT tablets were comparable to 1 mgA IR tablets given twice a day, and significantly superior to 2 mgA IR tablets given once daily.

EXAMPLE 3

Preparation of Preferred AMT CR Dosage Form for the L-Tartrate Salt of 1

A 7 kg batch of tableting granulation was prepared as follows: 1050 g of microcrystalline cellulose and 3340 g of calcium phosphate dibasic were mixed in an 16-quart V-blender for 20 min. To an 8-quart V-blender were added 2450 g of mannitol and 71.8 g of the drug. The mixture was mixed for 30 min. This material was added to the 16-quart V-blender (with the blend from the first blending process) and the mixture was blended for 30 mins (blend can be used to rinse blender to assure complete transfers). A 52.5 g aliquot of magnesium stearate was then added to the V-blender and the mixture was blended for 5 min. The mixture was roller compacted using a TF-Mini roller compactor with DSP rollers, using a roll pressure of 30 kg/cm², a roll speed of 4.0 rpm and an auger speed of 15 rpm resulting in ribbons with 0.06 to 0.08" thickness. The ribbons were milled using an M5A mill (available from Fitzpatrick Corp., Elmhurst, Ill.) with an 18 mesh Conidur rasping screen at 300 rpm. The powder was then placed back in the V-blender, and another 35 g of magnesium stearate were added, followed by an additional 5 min. of blending.

The granulation was tableted using a Kilian T100 tablet press using ⁹⁄₃₂" (11 mm) SRC tooling to give tablets of 250 mg/tablet (1.5 mgA). The precompression force used was 1.2 kN, the main compression force was 8 kN, running at 74 rpm with a feed paddle speed of 20 rpm. The resulting tablets showed hardnesses of 5-8 kp, with no measurable friability.

The tablets were coated by first preparing a coating solution consisting of 4095 g of cellulose acetate and 405 g of PEG in 30.6 kg of acetone and 9.9 kg of water. Coatings on 40,000 to 48,000 tablets per batch were carried out using an HCT-60 Hicoater (available from Vector Corp., Marion, Iowa). A spray rate of 180 g/min was maintained with an outlet temperature of 27° C. until the target coating weight of 13% gain was achieved. The tablets were then tray dried in an oven at 40° C. for 16 hrs.

Tablets showed pH independent dissolution behavior in vitro using USP type II dissolution (37° C., paddles at 50 rpm, analysis by HPLC potency assay). The percent of drug dissolved as a function of time in the dissolution medium were as follows: 2 hrs, 5%; 5 hrs, 30%; 7 hrs, 50%; 10 hrs, 70%; 12 hrs, 80%; 24 hrs, 97%. Thus the system delivers 0.1 mg/hr after a 2 hour lag.

EXAMPLE 4

Preparation of a Hydrophilic Matrix CR Dosage Form for the L-Tartrate Salt of 1

HPMC K4M (45.000 g) and 50.575 g of calcium phosphate dibasic were Turbula blended in a bottle for 10 min. Approximately 10 g of this blend were combined with 3.425 g of the L-tartrate salt of 1 and Turbula blended for 10 min. Remaining powder from the first mix was then added to drug containing blend and the combination was Turbula blended for 20 min. Magnesium stearate (1.000 g) was then added and the combination was blended for an additional 3 min. Tablets were prepared using a Manesty™ F-Press (single-punch tablet machine available from Manesty Corporation, Liverpool, UK) using ¼" SRC tooling. The average tablet weight was 102 mg/tablet corresponding to 0.5 mgA and the tablet hardness was 5-7 kp. In vitro dissolution experiments were carried out using simulated intestinal fluid (pH 6.8) at 37° C. using cages with sinkers on the tablets and paddles rotating at 50 rpm. The amount of drug dissolved over time was measured using an HPLC potency assay as follows: 2 hours, 59%; 4 hours, 85%; 8 hours, 94%; 16 hours, 97%. Thus the system delivered 0.10 mg/hour.

EXAMPLE 5

Preparation of a Hydrophobic Matrix CR Dosage Form for the L-Tartrate Salt of 1

A mixture of 0.86 g of 1 and 42.25 g of mannitol were passed through a #30 screen then Turbula blended for 2 min. Carnauba wax (6.04 g) and stearic acid (0.61 g) were added to a beaker and melted using a water bath at 90° C. While mixing, mannitol and drug blend were added to the melted wax and stearic acid mixture. The warm material was then screened through a #20 mesh screen, and then allowed to cool overnight. The material was combined with 0.09 g of silicon dioxide and Turbula blended for 2 min. Magnesium stearate (0.17 g) was added followed by an additional 0.5 min. Turbula blending. Tablets were prepared using 5/16" SRC tooling using an F-press to give a tablet weight of 200 mg (2 mgA).

EXAMPLE 6

Process Selection Based on Tablet Stability and Manufacturing Performance

This example compares conventional direct compression and wet granulation processes to dry granulation as the preferred method of processing. The dry granulation processing is presented using both a binary and ternary diluent formulation.

Dry Granulation:

The following ingredients were added to a bin blender, with drug layered in between excipients:

|  | Diluent System | |
| --- | --- | --- |
| Ingredient | Binary | Ternary |
| 1-L-tartrate | 0.87% | 0.57% |
| Mannitol | 0% | 26.02% |
| Microcrystalline cellulose (PH200) | 62.55% | 33.33% |
| Dibasic calcium phosphate | 33.33% | 33.33% |
| Croscarmellose sodium | 2.00% | 5.00% |
| Silicon dioxide (colloidal) | 0.50% | 0.50% |
| Magnesium stearate | 0.25% | 0.75% |
| Magnesium stearate | 0.50% | 0.50% |

The mixture was blended for 30 minutes. Magnesium stearate was added to the mixture and then blended for 3 minutes. The lubricated blend was roller compacted into ribbons using a roll pressure of 30 kg/cm², a roll speed of 4 rpm and an auger speed of 15 rpm (using a TF-Mini Roller Compactor (available from Vector Corp., Marion, Iowa). The ribbons were milled through a 20 mesh screen (Vector Rotary Granulator) to produce the granulation. The granulation was blended for 10 minutes. The second portion of magnesium stearate was added to the granulation and blended for 3 minutes. The final blend was compressed into 200 mg tablets using a Kilian T100 tablet press (Kilian & Co., Inc., Horsham, Pa.) fitted with 5/16 inch standard round concave punches.

Direct Compression (Comparative Process)

A binary diluent formulation (i.e. microcrystalline cellulose and dicalcium phosphate) was prepared with the levels listed below:

| 1-L-tartrate | 8.68 g |
| --- | --- |
| Microcrystalline cellulose | 621.27 g |
| Dibasic calcium phosphate | 333.30 g |
| Croscarmellose sodium | 20.00 g |
| Silicon dioxide (colloidal) | 5.00 g |

Two different blends were prepared and referred to as the "excipient pre-blend" and the "active pre-blend". The "excipient pre-blend" consisted of microcrystalline cellulose, silicon dioxide, and croscarmellose sodium. These ingredients were added to a V-blender and blended for 20 minutes. The active pre-blend consisted of drug and one-half of the dicalcium phosphate. The active pre-blend ingredients were added to a V-blender and blended for 30 minutes and discharged. One-half of the "excipient pre-blend" was added to a suitably sized blender followed by addition of the entire "active pre-blend" and then blended for 20 minutes. The second part of dicalcium phosphate was added to the empty blender used to mix the "active pre-blend" and mixed for 5 minutes. This and the second half of the "excipient pre-blend" were added to the blender containing the active. The mixture was blended for 20 minutes. Magnesium stearate (5.00 g) was added to the mixture and then blended for 5 minutes. The final blend was compressed into 200 mg tablets using a Kilian T100 tablet press (Kilian & Co., Inc., Horsham, Pa.) fitted with 5/16 inch standard round concave punches.

Wet Granulation (Comparative Formulations and Processes)

The wet granulation processing was evaluated with two different granulating agents, including water and isopropyl alcohol. The formulations prepared for each of the granulating agents are listed below:

|  | Granulating Agent | |
| --- | --- | --- |
| Ingredient |  | Isopropyl |
| 1-L-tartrate | 5.70 g | 5.70 g |
| Mannitol | 255.20 g | 260.20 g |
| Silicified microcrystalline cellulose | 333.30 g | — |
| Microcrystalline cellulose (PH200) | — | 333.30 g |
| Dibasic calcium phosphate | 333.30 g | 333.30 g |
| Hydroxypropyl cellulose | 10.00 g | — |
| Croscarmellose sodium | 50.00 g | 50.00 g |
| Water | 533.30 g | — |
| Isopropyl alcohol | — | 533.30 g |
| Silicon dioxide (colloidal) | 5.00 g | 5.00 g |
| Magnesium stearate | 7.50 g | 12.50 g |

The inactive ingredients listed above the granulating agent (water or isopropyl alcohol) in the formulation table were added to a high shear blender and dry mixed for 1 minute at 100 rpm impeller speed. One half of the excipient blend was removed from the bowl, and the total quantity of 1-L-tartrate was added to the blender and covered with the removed blend. This blend was mixed for 1 minute at 100 rpm. While continuing to blend, the granulating agent was added over 1 minute with chopper speed of 1000 rpm and impeller speed of 300 rpm. The wet granulation was mixed an additional 15 seconds following addition of the water or isopropyl alcohol. The wet mass was dried in a 50° C. oven to a moisture level within 1% of the initial value prior to granulating. The dried granulation was milled through a conical mill (Comil, Quadro Engineering, Inc., Waterloo, Ontario, Canada) fitted with a 0.050 inch screen and round edge impeller set at 1770 rpm. Colloidal silicon dioxide was added to this granulation and blended in a V-blender for 20 minutes. Magnesium stearate was added to the blender and blended for 5 minutes. The final blend was compressed into 300 mg tablets using a Kilian T100 tablet press (Kilian & Co., Inc., Horsham, Pa.) fitted with 11/32 inch standard round concave punches.

The blend uniformity of the direct compression and dry granulation processes is compared below. The batches utilized the same in-going bulk drug substance lot, drug loading (0.868%) and tablet size (200 mg). The potency and variability data are summarized in Table 5-1 below for the direct compression and dry granulation processes. The impact of dry granulating the formulation on blend uniformity is demonstrated by the reduction in blend variability from 8.0% to 1.8% RSD.

TABLE 6-1

| Manufacturing Process | Dry Granulation (binary) | Direct Compression |
|---|---|---|
| Percent Drug Load | 0.868 | 0.868 |
| Tablet Size (mg) | 200 | 200 |
| Final Blend Potency (avg) | 99.2 | 99.4 |
| Final Blend Potency (% RSD) | 1.8 | 8 |

The high variability (8% RSD) in the final blend potency prior to directly compressing the tablets was the basis for selecting dry granulation as the preferred process.

The wet and dry granulation processes were compared by manufacturing performance, in terms of granulation blend and tablet potencies and variabilities (percent relative standard deviation, or % RSD). These batches utilized the same in-going bulk drug substance lot, drug loading (0.57%) and tablet size (300 mg). The potency and variability data are summarized in Table 6-2 below for the three granulation processes evaluated here.

TABLE 6-2

| Manufacturing Process | Dry Granulation (ternary) | Wet Granulation with Water | Wet Granulation with IPO |
|---|---|---|---|
| Percent Drug Load | 0.57 | 0.57 | 0.57 |
| Tablet Size (mg) | 300 | 300 | 300 |
| Granulation Potency (avg) | 91.3 | 101.3 | 93.6 |
| Granulation Potency (% RSD) | 4.2 | 4.0 | 1.8 |
| Tablet Potency (avg) | | | |
| Beginning | 94.5 | 99.0 | 93.7 |
| Middle | 95.0 | 100.8 | 96.1 |
| End | 96.0 | 99.8 | 94.8 |
| Tablet (% RSD) | | | |
| Beginning | 1.2 | 2.5 | 2.3 |
| Middle | 0.4 | 0.9 | 0.4 |
| End | 1.2 | 2.6 | 1.0 |

Granulation and tablet potency values are closest to the intended 100% for the wet granulation process that used water as the granulating agent. The dry granulation and wet granulation with isopropyl alcohol processes resulted in similar manufacturing performance results.

Table 6-3 below summarized the stability results for tablets stored at the accelerated conditions for 6 weeks and analyzed by HPLC for the wet and dry granulation processes.

TABLE 6-3

| Manufacturing Process | Dry Granulation | Wet Granulation | Wet Granulation with |
|---|---|---|---|
| Percent Drug Load | 0.57 | 0.57 | 0.57 |
| Tablet Size (mg) | 300 | 300 | 300 |
| Total Percent Impurities After 6 Weeks: | | | |
| At 5° C. | ND | 0.08 | 0.30 |
| At 25° C./60% RH | ND | NA | NA |
| At 30° C./60% RH | NA | 0.10 | 0.35 |
| At 40° C./75% RH | 0 | 0.12 | 0.40 |
| At 50° C./20% RH | NA | 0.20 | 0.35 |
| Drug Form During | Anhydrous | Hydrate | Anhydrous |

Wet granulation using water as the granulating agent was found to be physically unstable due to a conversion from the anhydrous to hydrate state for the 1-L-tartrate. The hydrate was subsequently lost during the drying phase to form the anhydrous drug form. These physical stability changes during the wet granulation and drying process with water aided in the selection of the preferred process. Dry granulation and wet granulation with isopropyl alcohol are the preferred modes of processing for 1-L-tartrate tablets. The process that resulted in the lowest total impurity levels was dry granulation, followed by wet granulation with water and then wet granulation with isopropyl alcohol.

Therefore, the most preferred granulating process to make tablets of 1-L-tartrate based on stability, blend uniformity and manufacturing performance is dry granulation.

EXAMPLE 7

Diluent Selection Based on Tablet Stability

The diluents used in making 1-L-tartrate tablets were selected based on the chemical stability and manufacturing performance. Three diluents (dicalcium phosphate, microcrystalline cellulose, and mannitol) were evaluated using the preferred dry granulation processing, and included two (binary) or three (ternary) diluents in the formulation.

| | Diluents | |
|---|---|---|
| Ingredient | Dical/MCC/ Mannitol | MCC/ Mannitol |
| 1-L-tartrate | 0.57% | 0.57% |
| Mannitol | 26.02% | 42.68% |
| Microcrystalline cellulose (PH200) | 33.33% | 50.00% |
| Dibasic calcium phosphate | 33.33% | 0.0% |
| Croscarmellose sodium | 5.00% | 5.00% |
| Silicon dioxide (colloidal) | 0.50% | 0.50% |
| Magnesium stearate | 0.75% | 0.75% |
| Magnesium stearate | 0.50% | 0.50% |

Table 7-1 below summarizes the stability results for tablets prepared by dry granulation processing with either a ternary or binary (no dicalcium phosphate) formulation, stored for 3 months at accelerated conditions and analyzed by HPLC.

TABLE 7-1

| Manufacturing Process | Dry Granulation (ternary) | Dry Granulation (binary MCC/Mannitol - no Dical) |
|---|---|---|
| Percent Drug Load | 0.57 | 0.57 |
| Tablet Size (mg) | 300 | 300 |
| Total Percent Impurities After 6 Wks/3 Mos: | | |
| At 5° C. | ND/0 | 0/0.05 |
| At 25° C./60% RH | ND/0 | NA |
| At 30° C./60% RH | NA | 0.13/0.12 |
| At 40° C./75% RH | 0/0.10 | 0.28/0.34 |
| At 50° C./20% RH | NA | 0.23/0.58 |

NA indicates not applicable
ND indicates not detected

The formulation processed by dry granulation that resulted in the lowest total impurity levels utilized dicalcium phosphate. The preferred formulations prepared by dry granulation contain binary or ternary diluents of dicalcium phosphate, microcrystalline cellulose, and mannitol. The most preferred formulations prepared by dry granulation contain dicalcium phosphate as one of the major diluents.

Table 7-2 below summarized the stability results for tablets stored at the accelerated conditions for 6-12 weeks and analyzed by HPLC for the three binary diluent formulations to the ternary diluent formulation using the preferred dry granulation process.

TABLE 7-2

| Binary Diluents | MCC/Dical | Mannitol/Dical | Lactose/Dical | Ternary (Dical/MCC/Mannitol) |
|---|---|---|---|---|
| Percent Drug Load | 0.86 | 0.86 | 0.86 | 0.86 |
| Tablet Size (mg) | 200 | 200 | 200 | 300 |
| Total Percent Impurities After 6 and 12 Weeks: | | | | |
| At 5° C./75% RH | 0/0 | 0/0 | 0/NA | 0/0 |
| At 30° C./60% RH | 0.1/0.1 | 0/0 | 0.2/NA | 0.1/0.1 |
| At 40° C./75% RH | 0.1/0.3 | 0.1/0.2 | 2.6/NA | 0.1/0.3 |
| At 50° C./20% RH | 0.2/0.3 | 0.1/0.2 | 1.3/NA | 0.2/0.3 |

The lactose/dicalcium phosphate binary diluent formulation was found to be less stable under accelerated temperature/humidity conditions. The microcrystalline cellulose/dicalcium phosphate and mannitol/dicalcium phosphate binary tablets exhibited similar total impurity levels as the original ternary formulation, as shown in Table 7-2. Therefore, the ternary and MCC/Dical and mannitol/Dical binary systems are preferred embodiments of this invention.

EXAMPLE 8

Diluent Selection Based on Tablet Manufacturing Performance and Content Uniformity Based on chemical stability alone, the two binary formulations (MCC/Dical and mannitol/Dical) listed in Example 7 are suitable formulations of 1-L-tartrate. In order to select the more preferred composition, a manufacturing assessment was performed on a Kilian T-100 press with 3 stations of 5/16 inch SRC tooling. Tablets were compressed at 4, 8, 12, 16, and 20 kN force and tested for weight, thickness, hardness, disintegration time and % friability at each condition. Those data are listed below in Table 8-1.

The mannitol/dicalcium phosphate binary formulation exhibited severe capping issues and could not be tableted to a hardness above 3 kP, whereas the target range for this size tooling is 6-9 kP. At these hardnesses, the tablets had poor mechanical integrity based on the high % friability (desired less than 0.2%). Alternatively, the MCC/dicalcium phosphate binary tablet produced tablets with hardness and friability values within the target ranges. Therefore, the more preferred binary formulation based on the manufacturing assessment is microcrystalline cellulose/dicalcium phosphate. The ternary formulation is a preferred formulation based on stability and manufacturing, and is also an embodiment of this invention.

EXAMPLE 9

Disintegrant Selection Based on Tablet Stability

Tablets containing sodium starch glycolate (SSG) as a disintegrant were analyzed for purity and compared with croscarmellose sodium (CS) containing tablets. Tablets were placed 60 cc in HDPE/HIS bottles at 5° C./75% RH, 40° C./75% RH and 50° C./20% RH to be analyzed at 6 and 12 weeks. The 6 and 12 week purity results are shown in Table 9-1.

TABLE 9-1

| Stability Condition | Pull Point | Croscarmellose Sodium | Sodium Starch Glycolate |
|---|---|---|---|
| 5° C./75% RH | 6 Week | 0% | 0.3% |
| | 12 Week | 0% | 0.3% |
| 40° C./75% RH | 6 Week | 0.1% | 0.6% |
| | 12 Week | 0.3% | 0.9% |
| 50° C./20% RH | 6 Week | 0.2% | 0.9% |
| | 12 Week | 0.3% | 1.1% |

The degradation of the SSG tablets (0.3 to 1.1%) is greater than was observed for tablets containing CS as the disintegrant. These CS-containing tablets never exceeded 0.3% total degradation when lactose was not present in the tablet at any condition at 6 or 12 weeks. For this reason, croscarmellose sodium has been chosen as the more desirable disintegrant for

TABLE 8-1

| Lot # | Compression Force (kN) | Weight (mg) | Thickness (in.) | Hardness (kP) | Disintegration Time (min:sec) | Friability (%) |
|---|---|---|---|---|---|---|
| Mannitol/ | 4.53 | 199.8 | 0.150 | <1 | 00:17 | 35.48%[a] |
| Dical | 7.91 | 200.7 | 0.146 | 1.81 | 00:21 | 0.59% |
| | 11.65 | 200.1 | 0.141 | 2.73 | 00:19 | 0.34% |
| | 16.32 | 200.8 | 0.138 | 2.71 | 00:16 | 1.20%[b] |
| | 19.69 | 201.0 | 0.136 | 2.88 | 00:20 | 100%[c] |
| MCC/ | 3.94 | 201.5 | 0.156 | <1 | 00:04 | 100%[d] |
| Dical | 7.89 | 201.8 | 0.146 | 3.05 | 00:09 | 0.21% |
| | 11.51 | 202.0 | 0.139 | 4.84 | 00:12 | 0.11% |
| | 16.08 | 202.7 | 0.136 | 7.17 | 00:23 | 0.14% |
| | 17.56 | 201.5 | 0.135 | 7.91 | 00:13 | 0.067% |

[a]Two tablets were completely broken apart after testing.
[b]Two tablets capped during testing.
[c]All tablets capped during testing.
[d]All tablets broke apart during testing.

1-L-tartrate tablets based on the improved chemical stability compared to sodium starch glycolate.

EXAMPLE 10

Glidant Incorporated to Reduce Cohesivity of Blend

The impact of adding a glidant, colloidal silicon dioxide in this case, to the tablet formulation was evaluated using a standard powder avalanche test to characterize flow properties. For this evaluation, a placebo binary formulation was used since drug loading is less than 1%. The formulations are listed in Table 10-1. These tablets were prepared by the dry granulation method described in Example 6.

TABLE 10-1

|  | Glidant Content | |
| --- | --- | --- |
| Ingredient | 0% | 0.5% |
| Microcrystalline cellulose (PH200) | 63.42% | 62.92% |
| Dicalcium phosphate | 33.33% | 33.33% |
| Croscarmellose sodium | 2.00% | 2.00% |
| Silicon dioxide (colloidal) | 0.0% | 0.50% |
| Magnesium stearate | 0.75% | 0.75% |
| Magnesium stearate | 0.50% | 0.50% |

Blend and granulation were sampled immediately before each of the lubrication steps for analysis. The cohesivity, flow variability and particle size were evaluated and the results appear in Table 10-2. Granulation particle size of the two lots was very similar and thus should have had no effect on the powder avalanche results. Cohesivity and flow variability were improved by the presence of silicon dioxide. Its addition reduced cohesivity from 'low' to 'very low' rating for the blends and from 'high' to 'low' rating for the granulations. The presence of 0.50% silicon dioxide also reduced the granulation flow variability category from moderate to low.

TABLE 10-2

| Property | 0.5% Silicon Dioxide Blend | | 0.5% Silicon Dioxide Granulation | | 0% Silicon Dioxide Blend | | 0% Silicon Dioxide Granulation | |
| --- | --- | --- | --- | --- | --- | --- | --- | --- |
| Cohesivity (s) | 3.9 | Very Low Cohesivity | 4.5 | Low Cohesivity | 4.5 | Low Cohesivity | 6.1 | High Cohesivity |
| Flow Variability | 40.7 | Moderate Flow Variability | 31.1 | Low Flow Variability | 41.0 | Moderate Flow Variability | 41.1 | Moderate Flow Variability |
| D[4, 3] | 191.5 μm | | 161.0 μm | | 155.5 μm | | 160.5 μm | |

During tableting, the ejection force was monitored as a function of compression force. Table 10-3 lists the ejection forces resulting from compression forces in the range of 5-20 kN for the 0 and 0.5% silicon dioxide formulations.

TABLE 10-3

| Compression Force (kN) | 0% Ejection Force (N) | 0.5% Ejection Force (N) |
| --- | --- | --- |
| 6.3 | 29.56 | |
| 8.9 | 27.47 | |
| 12.2 | 25.88 | |
| 14.3 | 21.08 | |
| 18.6 | 21.56 | |
| 5.7 | | 16.64 |
| 9.1 | | 25.40 |
| 11.4 | | 22.58 |
| 15.0 | | 19.97 |
| 18.6 | | 23.56 |

The tablets containing 0.50% Cab-O-Sil showed a slightly lower ejection force over most of this compression range. Based on the positive attributes of reduced cohesivity, flow variability and ejection forces, 1-L-tartrate tablets containing a glidant is a more preferred formulation.

EXAMPLE 11

Film Coating Selection Based on Tablet Stability

The preferred white film coating for 1-L-tartrate tablets was selected based on chemical stability using accelerated challenge conditions. Four Opadry white film coating systems were applied onto one of the more preferred dry granulated tablet formulations.

The core tablets were made using a geometric dilution blending scheme prior to roller compacting, and contained the components listed below:

| | |
| --- | --- |
| 1-L-tartrate | 10.62 g |
| Microcrystalline cellulose | 744.42 g |
| Dibasic calcium phosphate | 399.96 g |
| Croscarmellose sodium | 24.00 g |
| Silicon dioxide (colloidal) | 6.00 g |
| Magnesium stearate | 9.00 g |
| Magnesium stearate | 6.00 g |

Two different blends were prepared and referred to as the "excipient pre-blend" and the "active pre-blend". The "excipient pre-blend" consisted of microcrystalline cellulose, silicon dioxide, and croscarmellose sodium. These ingredients were added to a V-blender and blended for 20 minutes. The "active pre-blend" consisted of drug and one-half of the dicalcium phosphate. The "active pre-blend" ingredients were added to a V-blender and blended for 30 minutes and discharged. One-half of the "excipient pre-blend" was added to a suitably sized V-blender, followed by addition of the entire "active pre-blend" and then blended for 20 minutes. The second part of dicalcium phosphate was added to the empty blender used to mix the "active pre-blend" and blended for 5 minutes. This and the second half of the "excipient pre-blend" were added to the blender containing the active. The mixture was blended for 20 minutes. The first portion of magnesium stearate was added to the mixture and then blended for 5 minutes. The lubricated blend was roller compacted into ribbons using a roll pressure of 30 kg/cm$^2$, a roll speed of 4 rpm and an auger speed of 15 rpm (Vector TF-Mini Roller Compactor). The ribbons were milled through a 20 mesh screen (Vector Rotary Granulator) to produce the granulation. The granulation was blended for 10 minutes. The second portion of magnesium stearate was added to the granulation and blended for 5 minutes. The final blend was compressed into 200 mg tablets using a Kilian T-100 tablet press (Kilian & Co., Inc., Horsham, Pa.) fitted with 5/16 inch standard round concave punches.

The qualitative compositions of the four coating systems are listed in Table 11-1. The coating composition listed as Lot Number A consisted of lactose, hydroxypropyl methylcellulose, or HPMC, titanium dioxide and triacetin. The main differences between the non-lactose coating systems, B through D, were the polymer type (hydroxypropyl methylcellulose, or HPMC, versus polyvinyl alcohol, or PVA) and the plasticizer type (polyethylene glycol, or PEG, and triacetin). The PVA coating also contained talc. The final dosage forms were coated to 4 wt % white coating and 0.5 wt % clear coating. Film coated tablets were placed in 60 cc HDPE/HIS bottles and challenged at 5° C. and 70° C./75% RH for 10 days and then evaluated for purity. Uncoated core tablets were also evaluated for comparison. Placebo tablets were prepared and analyzed for purity for the initial time point as a control. The purity results are shown in Table 11-2.

TABLE 11-1

| Coating Lot Number | Coating Components |
| --- | --- |
| A | Lactose Monohydrate<br>Hydroxypropyl Methylcellulose<br>Titanium Dioxide<br>Triacetin |
| B | Hydroxypropyl Methylcellulose<br>Titanium Dioxide<br>Triacetin |
| C | Hydroxypropyl Methylcellulose<br>Titanium Dioxide<br>Polyethylene Glycol |
| D | Polyvinyl Alcohol<br>Titanium Dioxide<br>Polyethylene Glycol<br>Talc |

The non-lactose based film-coated tablets containing HPMC (B and C) were found to be more chemically stable than either the lactose/HPMC (A) or PVA (D) film coated tablet. The total degradation of the HPMC lots was found to range from 0.4-1.2% and 0.5-1.0% for PEG and triacetin plasticizer, respectively. Meanwhile, the total degradation for the lactose control and PVA lots were as high as 3.5% and 2.9%, respectively. Based on the improved chemical stability, the preferred film coatings consist of HPMC, titanium dioxide and either triacetin or PEG in Formulation B and C, respectively.

TABLE 11-2

| Film Coating Identification | Placebo | Uncoated Tablet | A | B | C | D |
| --- | --- | --- | --- | --- | --- | --- |
| At 5° C. | 0.0* | 0.00 | 0.44 | 0.41 | 0.52 | 0.06 |
| At 70° C./75% RH | NA | 1.07 | 3.54 | 1.29 | 0.96 | 2.95 |

*indicates analysis was performed at the initial time point only

EXAMPLE 12

Process

Content Uniformity of Dry Granulation

This example demonstrates the more preferred blending processing to achieve blend and tablet potency and uniformity. V-blending (with and without geometric dilution), bin blending (with and without baffles and with straight vs. angled rotation) and high shear blending were evaluated. The formulation was composed of a binary diluent system of dicalcium phosphate and microcrystalline cellulose, as listed below:

| Component | % by Weight |
| --- | --- |
| 1-L-tartrate | 0.885 |
| Microcrystalline cellulose (PH200) | 62.035 |
| Dicalcium Phosphate dibasic (A-Tab) | 33.330 |
| Croscarmellose sodium | 2.00 |
| Silicon Dioxide (colloidal) | 0.50 |
| Magnesium stearate | 0.75 |
| Magnesium stearate | 0.50 |

V-Blending with Geometric Dilution

Formulation and process description for core tablet provided in Example 11.

V-Blending in Single Step

The mixture (without lubricant) was blended for 30 minutes. The first portion of magnesium stearate was added to the mixture and then blended for 5 minutes. The lubricated blend was roller compacted into ribbons using a roll pressure of 30 kg/cm$^2$, a roll speed of 4 rpm and an auger speed of 15 rpm (Vector TF-Mini Roller Compactor). The ribbons were milled through a 20 mesh screen (Vector Rotary Granulator) to produce the granulation. The granulation was blended for 10 minutes. The second portion of magnesium stearate was added to the granulation and blended for 5 minutes. The final blend was compressed into 200 mg tablets using a Kilian T100 tablet press (Kilian & Co., Inc., Horsham, Pa.) fitted with 5/16 inch standard round concave punches.

Bin Blending

The ingredients (without lubricant) were added to a bin blender with drug layered in the middle. The blender configuration (with or without baffles, and rotation straight or angled) was set-up. The mixture was blended for 30 minutes, the first portion of lubricant was added and blended for 5 minutes. The lubricated blend was roller compacted into ribbons using a roll pressure of 30 kg/cm$^2$, a roll speed of 4 rpm and an auger speed of 15 rpm (Vector TF-Mini Roller Compactor). The ribbons were milled through a 20 mesh screen (Vector Rotary Granulator) to produce the granulation. The granulation was bin blended for 10 minutes. The second portion of magnesium stearate was added to the granulation and blended for 5 minutes. The final blend was compressed into 200 mg tablets using a Kilian T100 tablet press (Kilian & Co., Inc., Horsham, Pa.) fitted with 5/16 inch standard round concave punches.

High Shear Blending

The ingredients (without lubricant) were added to a high shear blender with drug layered in the middle. The mixture was blended for 10 minutes with the impeller at 200 rpm and the chopper at 0 rpm. The first portion of lubricant was added and blended for 5 minutes. The lubricated blend was roller compacted into ribbons using a roll pressure of 30 kg/cm$^2$, a roll speed of 4 rpm and an auger speed of 15 rpm (Vector TF-Mini Roller Compactor). The ribbons were milled through a 20 mesh screen (Vector Rotary Granulator) to produce the granulation. The granulation was blended in a V-blender for 10 minutes. The second portion of magnesium stearate was added to the granulation and blended for 5 minutes. The final blend was compressed into 200 mg tablets using a Kilian T100 tablet press (Kilian & Co., Inc., Horsham, Pa.) fitted with 5/16 inch standard round concave punches.

The granulation and tablet potency and uniformity results are listed in Table 12-1. The V-blending in a single step and high shear blending processes resulted in the lowest granulation potency values. The more preferred blending process is blending with geometric dilution and bin blending with any configuration of baffles and rotation based on granulation and tablet potency and uniformity results. The high shear blender operated at low impeller speeds (low-to-moderate shear on this blender) is also a more preferred embodiment of this invention.

TABLE 12-1

| | Granulation | | Tablet | |
|---|---|---|---|---|
| Blending Process | Potency | % RSD | Potency | % RSD |
| V-blending with Geometric Dilution | 98.3 | 0.3 | 98.8 | 0.8 |
| V-blending in Single Step | 94.5 | 7.3 | 103.4 | 1.2 |
| Bin blending; no baffles, straight rotation | 99.1 | 1.2 | 101.7 | 0.8 |
| Bin blending; baffles, straight rotation | 100.3 | 0.7 | 102.7 | 1.4 |
| Bin blending; baffles, angled rotation | 98.3 | 1.0 | 102.1 | 0.6 |
| High shear blending | 91.1 | 0.4 | 96.2 | 2.3 |

EXAMPLE 13

Diluent Selection Based on Granulation Content Uniformity

The preferred diluent used in the "active pre-blend" for the geometric dilution blending process was selected based on granulation and tablet potency and uniformity. Two main diluents (dicalcium phosphate and mannitol) were investigated for their carrier excipient properties to aid in mixing of 1-L-tartrate within the formulation. The ingredients and levels used in the ternary tablet formulation (same composition as Example 7) were blended according to the geometric dilution scheme described in Example 11. The "active pre-blend" utilized either one half of the mannitol (13A) or dicalcium phosphate (13B). In this example, the drug was jet-milled to approximately half the original mean particle size prior to processing with excipients.

| | Diluent in "Active Pre-Blend" | |
|---|---|---|
| Ingredient | Mannitol (13A) | Dicalcium Phosphate (13B) |
| 1-L-tartrate (jet milled) | 0.86% | 0.86% |
| Mannitol | 25.95% | 25.95% |
| Microcrystalline cellulose (PH200) | 33.22% | 33.22% |
| Dibasic calcium phosphate (A-Tab) | 33.22% | 33.22% |
| Coscarmellose sodium | 5.00% | 5.00% |
| Silicon dioxide (colloidal) | 0.50% | 0.50% |
| Magnesium stearate | 0.75% | 0.75% |
| Magnesium stearate | 0.50% | 0.50% |

For each tablet formulation, two different blends were prepared and referred to as the "excipient pre-blend" and the "active pre-blend". The "excipient pre-blend" consisted of microcrystalline cellulose, silicon dioxide, croscarmellose sodium, and dicalcium phosphate or mannitol. These ingredients were added to a V-blender and blended for 20 minutes. The "active pre-blend" consisted of drug and approximately one-half of either mannitol (12A) or dicalcium phosphate (12B). The "active pre-blend" ingredients were added to a V-blender and blended for 30 minutes and discharged. One-half of the "excipient pre-blend" was added to a suitably sized V-blender, followed by addition of the entire "active pre-blend" and then blended for 20 minutes. The second part of mannitol or dicalcium phosphate was added to the empty blender used to mix the "active pre-blend" and blended for 5 minutes. This and the second half of the "excipient pre-blend" were added to the blender containing the active. The mixture was blended for 20 minutes. The first portion of magnesium stearate was added to the mixture and then blended for 5 minutes. The lubricated blend was roller compacted into ribbons using a roll pressure of 30 kg/cm$^2$, a roll speed of 4 rpm and an auger speed of 15 rpm (Vector TF-Mini Roller Compactor). The ribbons were milled through a 20 mesh screen (Vector Rotary Granulator) to produce the granulation. The second portion of magnesium stearate was added to the granulation and blended for 5 minutes. The final blend was compressed into 300 mg tablets using a Kilian T-100 tablet press (Kilian & Co., Inc., Horsham, Pa.) fitted with 11/32 inch standard round concave punches. The final granulation and tablet potency and variability (in terms of % RSD) results are listed in Table 13-1.

TABLE 13-1

| Carrier Excipient | 13A Mannitol 2080, granular | 13B Dibasic Calcium Phosphate, Anhyd. |
|---|---|---|
| Granulation Potency | Overall: 95.9% RSD: 0.2% | Overall: 96.3% RSD: 1.0% |
| Tablet Potency | Overall: 95.1% RSD: 2.4% | Overall: 97.2% RSD: 0.8% |

The granulation potency values are similar for both mannitol and dicalcium phosphate the "active pre-blend" diluent. However, the tablet potency values are increased from 95.1% to 97.2% when dicalcium phosphate replaced mannitol as the "active pre-blend" diluent used in the geometric dilution blending process. Therefore, the more preferred diluent used in the "active pre-blend" of the geometric dilution blending process is dicalcium phosphate.

What is claimed is:

1. A controlled release dosage form suitable for administration to a subject comprising 5,8,14-triazatetra-cyclo [10.3.1.0$^{2,11}$.0$^{4,9}$]-hexadeca-2(11),3,5,7,9-pentaene, or a pharmaceutically acceptable salt thereof, as a coated low dose tablet, said coated tablet comprising an asymmetric membrane system, wherein said low dose tablet is made of said pentaene, or pharmaceutically acceptable salt thereof, mannitol, microcrystalline cellulose, dicalcium phosphate, magnesium stearate, and less than 5 weight/weight percent reducing carbohydrate; wherein said low dose tablet contains from about 0.5 mgA up to about 6 mgA of said pentaene.

2. The controlled release dosage form of claim 1, wherein the pharmaceutically acceptable salt is an L-tartrate or a citrate salt.

3. The controlled-release dosage form of claim 1 wherein the dosage form is substantially free of reducing carbohydrates.

4. The controlled-release dosage of claim 1, wherein said coated tablet core comprises from about 30 to about 35 weight/weight percent mannitol, about 15 weight/weight percent microcrystalline cellulose, from about 47 to about 54 weight/weight percent dicalcium phosphate, about 1.5% weight/weight percent of magnesium stearate, and less than 5 weight/weight percent of a reducing carbohydrate.

5. The controlled-release dosage of claim 4, comprising about 35 weight/weight percent mannitol, about 15 weight/weight percent microcrystalline cellulose, about 48 weight/weight percent dicalcium phosphate, about 1.5% weight/weight percent of magnesium stearate, and less than 5 weight/weight percent of a reducing carbohydrate, having a controlled-release coating.

6. The controlled-release dosage form of claim 4, wherein the coating comprises cellulose acetate.

7. The controlled-release dosage form of claim 4, wherein the pharmaceutically acceptable salt is an L-tartrate or a citrate salt.

* * * * *